United States Patent

Haas et al.

[11] Patent Number: 6,057,355
[45] Date of Patent: May 2, 2000

[54] PESTICIDAL COMBINATION

[75] Inventors: Charles Lee Haas, Garner; Michael Thomas Pilato, Cary; Philip Reid Timmons, Durham; Tai-Teh Wu, Chapel Hill; Scot Kevin Huber; Bernard Leroux, both of Raleigh, all of N.C.

[73] Assignee: Rhone-Poulenc Inc., Research Triangle Park, N.C.

[21] Appl. No.: 09/058,359

[22] Filed: Apr. 10, 1998

Related U.S. Application Data

[60] Provisional application No. 60/054,795, Aug. 5, 1997.

[30] Foreign Application Priority Data

Mar. 5, 1998 [WO] WIPO .................. PCT/EP98/01224

[51] Int. Cl.[7] .................. A01N 43/56; A01N 47/28
[52] U.S. Cl. .................. 514/404; 514/594
[58] Field of Search .................. 514/404, 594

[56] References Cited

U.S. PATENT DOCUMENTS

| | | | |
|---|---|---|---|
| 4,973,589 | 11/1990 | Barnett et al. | 514/245 |
| 5,135,953 | 8/1992 | Potter et al. | 514/594 |
| 5,232,940 | 8/1993 | Hatton et al. | 514/407 |
| 5,236,938 | 8/1993 | Huang et al. | 514/341 |
| 5,416,102 | 5/1995 | Barnett et al. | 514/351 |
| 5,567,429 | 10/1996 | Senbo | 424/405 |

FOREIGN PATENT DOCUMENTS

| | | |
|---|---|---|
| 0255803 | 2/1988 | European Pat. Off. . |
| 0295117 | 12/1988 | European Pat. Off. . |
| 0385809 | 9/1990 | European Pat. Off. . |
| 0403300 | 12/1990 | European Pat. Off. . |
| 0679650 | 11/1995 | European Pat. Off. . |
| 2713889 | 6/1995 | France . |
| 195 11 269 | 10/1995 | Germany . |
| 19548874 | 7/1997 | Germany . |
| 2317564 | 4/1998 | United Kingdom . |
| 86/03941 | 7/1986 | WIPO . |
| 86/05780 | 10/1986 | WIPO . |
| 87/03781 | 7/1987 | WIPO . |
| 93/06089 | 4/1993 | WIPO . |
| 94/21606 | 9/1994 | WIPO . |
| 95/33380 | 12/1995 | WIPO . |
| 97/36485 | 10/1997 | WIPO . |

OTHER PUBLICATIONS

Colby, S.R., "Calculating Synergistic and Antagonistic Responses of Herbicide Combinations", *Weeds*, 15, pp. 20–22 (1967).

*Primary Examiner*—Allen J. Robinson
*Attorney, Agent, or Firm*—Burns, Doane, Swecker & Mathis, L.L.P.

[57] ABSTRACT

A pesticidal combination comprising a compound of formula (I) and a 1-arylpyrazole of formula (II).

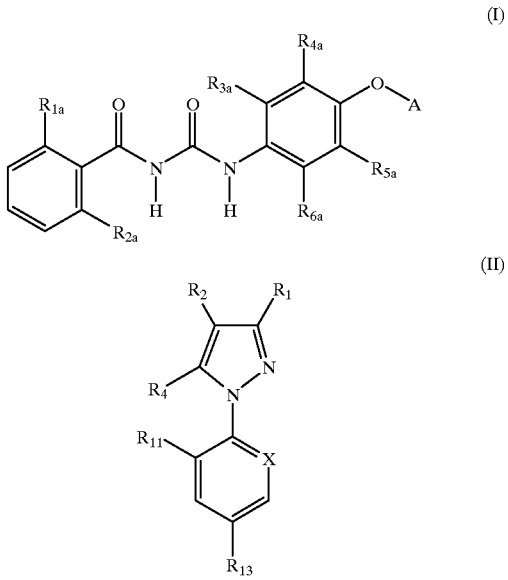

64 Claims, No Drawings

PESTICIDAL COMBINATION

CROSS-REFERENCE TO RELATED APPLICATION

This application claims the priority of United States Provisional Patent Application No. 60/054,795, filed Aug. 5, 1997, incorporated by reference herein in its entirety and relied upon.

CROSS-REFERENCE TO PRIORITY APPLICATION

This application claims priority under 35 U.S.C. §119 of International PCT Application No. PCT/EP98/01224, filed Mar. 5, 1998, incorporated by reference herein in its entirety and relied upon.

BACKGROUND OF THE INVENTION

1. Technical Field of the Invention

The present invention relates to a new pesticidal combination, a composition comprising the combination and to a method of controlling pests. The invention further relates to a process for the preparation of the novel composition, to the use thereof and to plant propagation material treated therewith, and to the use of a compound of formula (I) below for the preparation of said novel composition.

2. Background Art

Certain mixtures of pesticides have been proposed in the literature for pest control. However, the biological properties of these known mixtures are unable to satisfy the requirements made of them in the field of pest control in all respects, so that there is still a need to provide further mixtures having synergistic properties for pest control, in particular for controlling insects and representatives of the orders. In particular, the problem in the control of pests in animals is the necessity to provide repeated doses in an animal over a short time period. Such repeated dosing exposes the animal owner or keeper to the pesticide.

SUMMARY OF THE INVENTION

Thus there exists a need to provide more long-lasting pesticidal treatments, preferably with doses of pesticide at or below those generally used in the art. This need is met in whole or in part by the provisions of this invention.

Accordingly, the invention relates to a pesticidal combination comprising a compound of formula (I):

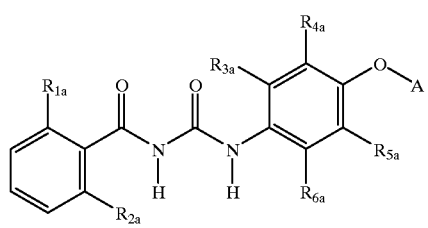

wherein:

$R_{1a}$ and $R_{2a}$ are, independently of each other, hydrogen or halogen;

$R_{3a}$ is hydrogen, chlorine or alkyl;

$R_{4a}$ $R_{5a}$ and $R_{6a}$ are, independently of one another, alkyl, preferably methyl, hydrogen or halogen;

A is G1, G2, G3 or G4:

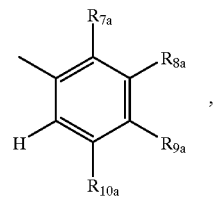

(G1)

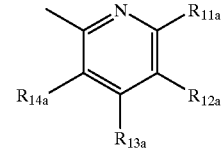

(G2)

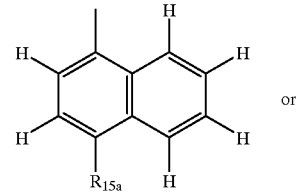

(G3)

or

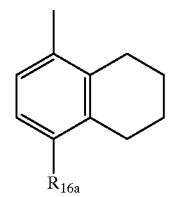

(G4)

wherein $R_{7a}$ to $R_{16a}$ are, independently of one another, hydrogen, halogen, alkyl or nitro; and provided that $R_{1a}$ and $R_{2a}$ are not simultaneously hydrogen; and that $R_{4a}$, $R_{5a}$ and $R_{6a}$ are not simultaneously hydrogen;

in the free form or in the form of a pesticidally acceptable salt thereof, and a 1-arylpyrazole of formula (II):

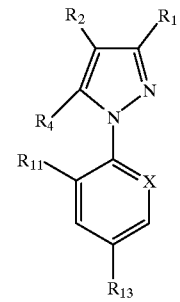

(II)

wherein:

$R_1$ is CN or methyl;

$R_2$ is $S(O)_n R_3$;

$R_3$ is alkyl or haloalkyl;

$R_4$ is hydrogen, halogen, —$NR_5R_6$, —$C(O)OR_7$, —$S(O)_m R_7$, alkyl, haloalkyl, —$OR_8$, —$N=C(R_9)$ ($R_{10}$) or —$C(O)$alkyl;

$R_5$ and $R_6$ are, independently of each other, hydrogen, alkyl, haloalkyl, —C(O)alkyl, —C(O)OR$_7$ or —S(O)$_r$CF$_3$; or $R_5$ and $R_6$ form together a divalent alkylene radical which is optionally interrupted by one or more heteroatoms, each of which is preferably oxygen, nitrogen or sulfur;

$R_7$ is alkyl or haloalkyl;

$R_8$ is alkyl, haloalkyl or hydrogen;

$R_9$ is hydrogen or alkyl;

$R_{10}$ is phenyl or heteroaryl, each of which is optionally substituted by one or more hydroxy, halogen, —O—alkyl, —S—alkyl, cyano, or alkyl or combinations thereof;

X is nitrogen or C-R$_{12}$; $R_{11}$ and $R_{12}$ are, independently of each other, halogen or hydrogen; $R_{13}$ is halogen, haloalkyl, haloalkoxy, —S(O)$_q$CF$_3$ or —SF$_5$;

m, n, q, r are, independently of one another, 0, 1 or 2;

provided that when $R_1$ is methyl, then $R_3$ is haloalkyl, $R_4$ is NH$_2$, $R_{11}$ is Cl, $R_{13}$ is CF$_3$, and X is N.

DETAILED DESCRIPTION OF THE INVENTION AND PREFERRED EMBODIMENTS

The alkyl groups of formula (I) are optionally substituted by one or more halogens.

The alkyl and alkoxy groups and moieties of the formula (II) are preferably lower alkyl and alkoxy groups, that is, groups having one to four carbon atoms. The haloalkyl and haloalkoxy groups likewise preferably have one to four carbon atoms. The haloalkyl and haloalkoxy groups can bear one or more halogen atoms; preferred groups of this type include —CF$_3$ and —OCF$_3$. It shall be understood that the ring formed by the divalent alkylene radical represented by $R_5$ and $R_6$ and including the nitrogen atom to which $R_5$ and $R_6$ are attached is generally a 5, 6, or 7-membered ring. It will be understood that the compounds of formula (I) and the 1-phenylpyrazoles of formula (II) include enantiomers and/or diastereomers thereof. The invention embraces these and mixtures thereof.

A preferred group of compounds of formula (I) for use in the present invention are those with one or more of the following features wherein:

$R_{1a}$ and $R_{2a}$ are independently selected from halogen, preferably chlorine or fluorine;

A is G1;

$R_{3a}$ is methyl;

$R_{4a}$, $R_{5a}$ and $R_{6a}$ are independently hydrogen, halogen, preferably chlorine, or methyl; or $R_{7a}$, $R_{8a}$, $R_{9a}$ and $R_{10a}$ are independently selected from hydrogen and halogen.

A preferred group of 1-arylpyrazoles for use in the present invention are those of formula (II) with one or more of the following features:

$R_1$ is CN;

$R_4$ is —NR$_5$R$_6$;

$R_5$ and $R_6$ are independently selected from hydrogen, alkyl, haloalkyl, C(O)alkyl and C(O)OR$_7$;

X is C-R$_{12}$;

$R_{13}$ is selected from halogen, haloalkyl, haloalkoxy, and —SF$_5$.

A particularly preferred group of 1-arylpyrazoles for use in the present invention are those of formula (II) wherein:

$R_1$ is CN;

$R_4$ is —NR$_5$R$_6$;

$R_5$ and $R_6$ are independently selected from the hydrogen atom, alkyl, haloalkyl, C(O)alkyl, C(O)OR$_7$;

X is C-R$_{12}$; and $R_{13}$ is selected from a halogen atom, haloalkyl, haloalkoxy, and —SF$_5$.

According to the present invention a very particularly preferred compound of formula (II) is 5-amino-(2,6-dichloro-α,α,α-trifluoro-p-tolyl)-4-trifluoromethylsulfinylpyrazole-3-carbonitrile, known as fipronil. Fipronil is also known by the chemical name 5-amino-3-cyano-1-(2,6-dichloro-4-trifluoromethylphenyl)-4-trifluoromethylsulfinylpyrazole.

A preferred combination is that of a compound of formula (I) and a 1-arylpyrazole of formula (II) wherein $R_1$ is CN, $R_2$ is —S(O)Et, $R_{11}$ is Cl, X is C-Cl, $R_{13}$ is CF$_3$ and $R_4$ is selected from —NH$_2$, —NHMe or —NHEt, particularly 5-amino-(2,6-dichloro-α,α,α-trifluoro-p-tolyl)-4-ethylsulfinylpyrazole-3-carbonitrile also known as Compound B. Compound B can also be named 5-amino-3-cyano-1-(2,6-dichloro-4-trifluoromethylphenyl)-4-ethylsulfinylpyrazole.

A particularly preferred combination is that of a compound of formula (I) wherein $R_{1a}$=$R_{2a}$=F; $R_{3a}$=$R_{5a}$=Me; $R_{4a}$=Cl; $R_{6a}$=H; A=G1; $R_{7a}$=$R_{9a}$=Cl; $R_{8a}$=$R_{10a}$=H, also called 1-[4-(2,4-dichlorophenoxy)-2,5-dimethyl-3-chlorophenyl]-3-(2,6-difluorobenzoyl)urea, hereinafter known as Compound (C); and a compound of formula (II).

The general preparation of compounds of formula (I) may be found in U.S. Pat. No. 5,135,953, incorporated by reference herein in its entirety and relied upon, and references recited therein.

The preparation of compounds of formula (II) is described in International Patent Publications No. WO 87/03781, WO 93/06089 and WO 94/21606, as well as in European Patent Publication numbers 0295117, 0403300, 0385809, and 0679650, German Patent Publication 19511269 and U.S. Pat. Nos. 5,232,940 and 5,236,938, and prior copending U.S. patent application Ser. No. 08/768,120, filed Dec. 17, 1996, all of which are incorporated by reference herein in their entireties and relied upon.

The pesticidally acceptable salts of the compound of formula (I) are typically addition salts of inorganic and organic acids, preferably of hydrochloric acid, hydrobromic acid, sulfuric acid, nitric acid, perchloric acid, phosphoric acid, formic acid, acetic acid, trifluoroacetic acid, oxalic acid, malonic acid, toluenesulfonic acid or benzoic acid.

Preferred combinations within the scope of this invention are those that contain the compound of formula (I) in the free form as an active ingredient.

A combination of the compound of formula (I) and only one 1-arylpyrazole of formula (II) is also preferred.

Other compounds of formula (I) which may be used in the present invention are those listed in Table (I).

TABLE 1

| Cmpd. No. | $R_{1a}$ | $R_{2a}$ | $R_{3a}$ | $R_{4a}$ | $R_{5a}$ | $R_{6a}$ | A | $R_{7a}$ | $R_{8a}$ | $R_{9a}$ | $R_{10a}$ | $R_{11a}$ | $R_{12a}$ | $R_{13a}$ | $R_{14a}$ | $R_{15a}$ |
|---|---|---|---|---|---|---|---|---|---|---|---|---|---|---|---|---|
| 1 | F | F | H | Cl | Cl | H | G2 | — | — | — | — | H | $CF_3$ | H | Cl | — |
| 2 | F | F | H | Cl | Cl | H | G1 | H | H | $NO_2$ | H | — | — | — | — | — |
| 3 | F | F | H | Cl | Cl | H | G3 | — | — | — | — | — | — | — | — | Cl |
| 4 | F | F | H | H | $CF_3$ | H | G3 | — | — | — | — | — | — | — | — | Cl |
| 5 | F | F | H | H | $CH_3$ | H | G3 | — | — | — | — | — | — | — | — | Cl |
| 6 | F | F | H | H | H | H | G3 | — | — | — | — | — | — | — | — | Cl |
| 7 | F | F | $CH_3$ | H | $CH_3$ | H | G3 | — | — | — | — | — | — | — | — | Cl |
| 8 | H | Cl | $CH_3$ | Cl | $CH_3$ | H | G3 | — | — | — | — | — | — | — | — | Cl |
| 9 | F | F | H | Cl | Cl | H | G2 | — | — | — | — | H | Cl | H | Cl | — |
| 10 | F | F | $CH_3$ | H | Cl | H | G3 | — | — | — | — | — | — | — | — | Cl |
| 11 | Cl | H | $CH_3$ | Cl | $CH_3$ | H | G1 | $CH_3$ | H | $CH_3$ | H | — | — | — | — | — |
| 12 | F | F | $CH_3$ | Cl | $CH_3$ | H | G1 | $CH_3$ | H | Cl | $CH_3$ | — | — | — | — | — |
| 13 | F | F | $CH_3$ | Cl | $CH_3$ | H | G1 | $CH_3$ | $CH_3$ | Br | H | — | — | — | — | — |
| 14 | F | F | H | Cl | Cl | H | G1 | H | H | Cl | H | — | — | — | — | — |
| 15 | F | F | $CH_3$ | Cl | $CH_3$ | H | G1 | Cl | H | Cl | H | — | — | — | — | — |
| 16 | F | F | Cl | Cl | H | Cl | G3 | — | — | — | — | — | — | — | — | Cl |
| 17 | F | H | $CH_3$ | Cl | $CH_3$ | H | G1 | Br | H | Cl | H | — | — | — | — | — |
| 18 | F | F | $CH_3$ | Cl | $CF_2H$ | H | G3 | — | — | — | — | — | — | — | — | Cl |
| 19 | F | F | $CH_3$ | Cl | $CH_3$ | H | G3 | — | — | — | — | — | — | — | — | Cl |

The pesticidal combination of this invention will preferably contain the compound of formula (I) and 1-arylpyrazole in a weight ratio of 1:50 to 50:1, especially in a ratio from 1:20 to 20:1, more particularly from 10:1 to 1:10, still more particularly from 5:1 to 1:5, very particularly from 2:1 to 1:2, for example in the ratio 1:1. Another useful weight ratio of (I) to (II), of special interest when (II) is Compound B, is from about 1:625 to 1:333,334.

The combination of the pesticide of formula (I) and the 1-arylpyrazoles of formula (II) provides a generally long acting effect, generally from 30 to 180 days, preferably from 180 to 240 days, more preferably from 240 to 300, and most preferably from 300 to 360 days after treatment. An additive enhancement of the activity spectrum on the pests to be controlled can also be obtained. The combination can also provide a synergistic effect that potentiates the activity ranges of both compounds from two points of view.

On the one hand, the concentrations of the compound of formula (I) and the 1-arylpyrazoles of formula (II) are reduced with no reduction in the activity obtained. On the other hand, the combination also achieves a high degree of pest control where the individual compounds are substantially or completely inactive at low concentrations. This feature permits on the one hand a broadening of the activity spectrum against the controllable pests and, on the other, an enhancement of safety of application.

The combinations of the invention also have a useful antifeeding effect. Such an antifeeding effect is generally not seen with the individual compounds of formula (I) or salts thereof. An antifeeding effect is advantageous in that regardless of the killing action of the active ingredients, the plant is protected from damage and therefore may provide effective protection to the locus so treated with the active ingredient.

The combinations of this invention have useful preventive and/or curative properties in the field of pest control even at low concentration. They are well tolerated by warm-blooded animals, fish and plants, and they have a very favorable biocidal spectrum. The compositions are effective against all, or individual, development stages of normally sensitive as well as resistant pests of animals such as insects and representatives of the order Acarina. The onset of the insecticidal and/or acaricidal action of the novel compositions may follow directly, i.e. a kill of the pests will occur immediately or only after some time, for example where moulting is effected, or indirectly, for example in diminished oviposition and/or hatching rate.

The mixtures of the invention are most valuable because of their long term effect as well as because of their good margin of safety for veterinary and nuisance insect applications. They are also most useful because of their combined activity on parasites, preferably on both ticks and fleas, especially those of pets, such as dogs or cats, particularly cats. The combination of the compounds of formula (II) with a compound of formula (I), especially compound (C), therefore generally provides a solution to the problem of flea and tick control.

Generally, one administration per week, preferably one administration per month, more preferably one administration every two to three months, even more preferably one administration every four to six months, even more preferably one administration every seven to eight months, and most preferably every nine to twelve months or higher provide generally good efficacy.

Another advantage of the combination of the invention is that it is well adapted to oral administration or administration by injection, particularly subcutaneous injection or by subcutaneous implant which methods are generally known to those skilled in the art. The appropriate doses are generally from 5 to 50 mg/kg, preferably 10 to 30 mg/kg of the compound of formula (II), "mg/kg" in this instance indicating the milligrams of compound of formula (II) per kilogram of body weight of animal. The amount the compound of formula (I) compound present in the mixture will vary according to the efficacy of the active ingredient and the precise conditions of use and is generally from 1 to 100 mg/kg, preferably from 5 to 80 mg/kg, more preferably from 10 to 50 mg/kg, and most preferably from 10 to 20 mg/kg.

The term "parasites" as used in the specification and claims is meant to encompass all endoparasites and ectoparasites of warm-blooded animals as well as pests that breed in the manure of the animals.

The aforementioned animal pests typically include:
of the order Lepidoptera,

Acleris spp., Adoxophyes spp., Aegeria spp., Agrotis spp., *Alabama argulaceae,* Amylois spp., *Anticarsia gemmatalis,* Archips spp., Argyrotaenia spp., Autographa spp., *Busseola fusca, Cadra cautella, Carposina nipponensis,* Chilo spp., Choristoneura spp., *Clysia ambigueua,* Cnaphalocrocis spp., Cnephasia spp., Cochylis spp., Coleophora spp., *Crocido-*

*lomia binotaus, Cryptophlebia leucotreta,* Cydia spp., Diatraea spp., *Diparopsis castanea,* Earias spp., Ephestia spp., Eucosma spp., *Eupoecilia ambiguena,* Euproctis spp., Euxoa spp., Grapholita spp., *Hedya nubiferana,* Heliothis spp., *Hellula andalis, Hyphantria cunea, Keiferia lycopersicella, Leucoptera scitella,* Lithocllethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypieua, Phthorimaea operculeua, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

of the order Coleoptera, for example,

Agriotes spp., Anthonomus spp., Atomaria linearis, Chaetocnema tibialis, Cosmopolites spp., Curculio spp., Dermestes spp., Diabrotica spp., Epilachna spp., Eremnus spp., *Leptinotarsa decemlineata,* Lissorhoptrus spp., Melolontha spp., Oryzaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

of the order Orthoptera, for example,

Blatta spp., Blattella spp., Gryllotalpa spp., *Leucophaea maderae,* Locusta spp., Periplaneta spp. and Schistocerca spp.;

of the order Isoptera, for example,

Reticulitermes spp.;

of the order Psocoptera, for example,

Liposcelis spp.;

of the order Anoplura, for example,

Haematopinus spp., Linognathus spp., Pediculus spp., Pemphigus spp. and Phylloxera spp.;

of the order Mallophaga, for example, Damalinea spp. and Trichodectes spp.;

of the order Thysanoptera, for example,

Frankliniella spp., Hercinothrips spp., Taeniothrips spp., *Thrips palmi, Thrips tabaci* and *Scirtothrips aurantii;* of the order Heteroptera, for example,

Cimex spp., Distantiella theobroma, Dysdercus spp., Euchistus spp, Eurygaster spp., Leptocorisa spp., Nezara spp., Piesma spp., Rhodnius spp., *Sahlbergella singularis,*

Scotinophara spp. and Triatoma spp.;

of the order Homoptera, for example,

*Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma lanigerum,* Erythroneura spp, Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylia spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* of the order Hymenoptera, for example,

Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

of the order Diptera, for example,

Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp, Oestrus spp., Orseolia spp., Oscinella frit, *Pegomyia hyoscyami,* Phorbia spp., *Rhagoletis pomonella,* Sciara spp., Stomoxys spp., Tabanus spp., Tannia spp. and Tipula spp.;

of the order Siphonaptera, for example,

Ceratophyllus spp. and Xenopsylla cheopis;

of the order Thysanura, for example,

*Lepisma saccharina;* and of the order Acarina, for example,

*Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptrum oleivora, Polyphagotarsonemus latus,* Psoroptes spp., Rhipicephalus spp., Rhizoglyphus spp., Sarcoptes spp., Tarsonemus spp. and Tetranychus spp.

Within the scope of this invention it is possible to control in particular pests:

(1) of the order Lepidoptera, especially Adoxophyes spp., *Alabama argillaceae, Clysia ambigulla, Clysia pomonelia, Crocidolomia binotalis,* Cydia spp., Earias spp., Heliothis spp., *Lobesia botrana, Ostrinia nubilalis, Phthohmea operculeua,* Sparganothis spp. and Spodoptera spp.;

(2) of the order Coleoptera, in particular the family Curculionidae, more particularly Anthonomus spp., more particularly still A. grandis, very particularly the family Chrysomelidae, most preferably *Leptinotarsa decemlineata;*

(3) of the order Homoptera, in particular the family Aphididae, more particularly the genus Aphis, most particularly A. gossypii; in particular the family Aleurodidae, preferably *Aleurothrixus floccus* and *Bemisia tabaci;* in particular Fainilie Psyllidae, more preferably Psylla spp.;

(4) of the order Thysanoptera, in particular the family Thripidae, preferably Frankliniella spp., Thrips palmi and Thrips tabaci;

(5) of the order Acarina, in particular the family Eriophyidae, more particularly *Aculus schlechtendali* and *Phyllocoptruta oleivora;*

(6) of the order Diptera, in particular the family Agromyzidae, more particularly *Liriomyza trifolii;*

(7) of the order Isoptera, Reticulitermes spp.; and (8) of the order Orthoptera, Blattella spp. and Periplaneta spp.

Preferably, representative parasites which may be controlled by the method of this invention include members of the Arthropoda (Arthropods), including mites in suborder Mesostigmata, Sarcoptiformes, Trombidiformes and Onchychopalpida; sucking and biting lice in orders Anoplura and Mallophaga; ticks in the families Ixodidae and Argasidae; fleas in the families Pulicidae, Ceratophyllidae, and others; Cimex and other Hemiptera; Triatominae and other Heteroptera; and myiasis-related fly larvae and blood sucking adults (including mosquitoes) in the suborders Brachycera, Cyclorrhapha and Nematocera. Representative also are helminths included in the Nematoda (Strongylidia, including but not limited to Strongyloidea, Ancylostomatoidea, Trichostrongyloidea and Metastrongyloidea; Ascarida [Ascaris]; Filariina, such as but not limited to Onchocerca and Dirofilaria; Rhabditida; and trichinellida); Cestoidea, especially Cyclophyllidea, and Trematoda, including Strigeatoidea such as Schistosoma; Echinostomida such as Fasciola; and Plagiorchiida such as Para yonimus. Other parasites which may be controlled by compounds represented by generic formula (I) include Acanthocephala such as Macracanthorhynchus or Moniliformis, and Pentastomida, especially Liguatula; and protozoa, especially Coccidia such as Eimeria and Plasmodium, Piroplasmea such as Babesia; Toxoplasmea such as Tripanosoma; Trichomonadidae such as Trichomonas and Entamoebidae such as Entamoeba.

Illustrative of specific parasites of various host animals which may be controlled by the method of this invention are arthropods such as mites (mesostigmatids, itch, mange, scabies, chiggers), ticks (soft-bodied and hard-bodied), lice (sucking, biting), fleas (dog flea, cat flea, oriental rat flea, human flea), true bugs (bed bugs, Triatomid bugs), blood-sucking adult flies (horn fly, horse fly, stable fly, black fly, deer fly, louse fly, tsetse fly, mosquitoes), and parasitic fly maggots (bot fly, blow fly, screwworm, cattle grub, fleeceworm); helminths such as nematodes (threadworm, lungworm, hookworm, whipworm, nodular worm, stomach worm, round worm, pinworm, heartworm), cestodes (tapeworms) and trematodes (liver fluke, blood fluke); protozoa such as coccidia, trypanosomes, trichmonads, amoebas and plasmodia; acanthocephalans such as thorny-headed worms (lingulatulida); and pentastomids such as tongue-worms.

With the novel pesticidal combinations it is possible to control, i.e. inhibit or destroy, in particular pests of the above mentioned type that occur in plants, especially in cultivated plants and ornamentals, in horticulture and in forestry, or in parts of such plants such as fruit, blossoms, leaves, stems, tubers or roots, while in some cases parts of plants that grow later can also be protected against these pests.

The pesticidal combination of this invention can be used with advantage for pest control in cereals such as maize or sorghum; fruit such as pome fruit, stone fruit and soft fruit, typically apples, pears, plums, peaches, almonds, cherries, or berries, for example strawberries, raspberries and blackberries; leguminous plants, typically including beans, lentils, peas and soybeans; oil plants such as rape, mustard, poppy, olives, sunflowers, coconut, castor oil plants, cocoa beans and groundnuts; cucurbits such as marrows, cucumber and melons; fiber plants such as cotton, flax, hemp and jute; citrus fruit such as oranges, lemons, grapefruit and mandarins; vegetables such as spinach, lettuce, asparagus, cabbages, carrots, onions, tomatoes, potatoes and paprika; lauraceae such as avocados, cinnamon and camphor, and tobacco, nuts, coffee, egg plants, sugar cane, tea, pepper, vines, hops, bananas and natural rubber plants or ornamentals, in particular in maize, sorghum, pome fruit, stone fruit, leguminous plants, cucurbits, cotton, citrus fruit, vegetables, eggplants, vines, hops or ornamentals; preferably in maize, sorghum, apples, pears, plums, peaches, peas, soybeans, olives, sunflowers, coconuts, cocoa beans, cabbages, tomatoes, potatoes, vines or cotton; and, most preferably, in vines, citrus fruit, apples, pears, tomatoes and cotton.

Further utilities of the pesticidal combinations of this invention are the protection of stored goods and materials as well as in the hygiene sector, for example, domestic animals and productive livestock against pests of the indicated type.

The method of the present invention comprises known methods of application of the combination of the invention to the domestic animal including spraying, rubbing, application by spotting, dip, collar, ear tag, or orally. Preferably, the combinations of the invention are administered orally (that is, into the digestive tract) or via injection. Most preferably the combinations are administered orally via a bolus.

According to the present invention, the frequency of treatment of the domestic animal to be treated by the compound of formula (I) is generally from about once per week to about once per year, preferably from about once every two weeks to about once every six months, and most preferably from about once per month to about once every three months.

The present invention also relates to a use of a combination comprising a compound of formula (I)

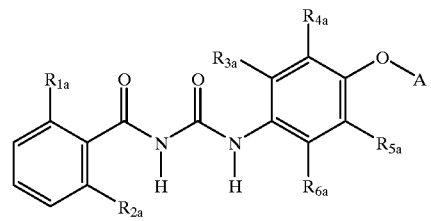

wherein:
$R_{1a}$ and $R_{2a}$ are, independently of each other, hydrogen or halogen;
$R_3a$ is hydrogen, chlorine or alkyl;
$R_{4a}$, $R_{5a}$ and $R_{6a}$ are, independently of one another, alkyl, preferably methyl, hydrogen or halogen;
A is G1, G2, G3 or G4:

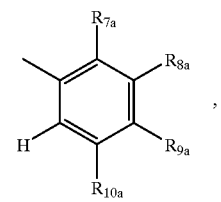
(G1)

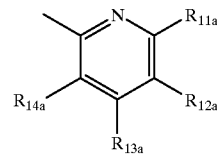
(G2)

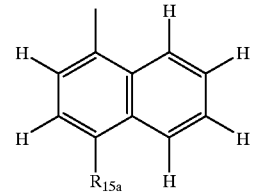
or
(G3)

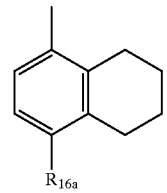
(G4)

wherein
$R_{7a}$ to $R_{16a}$ are, independently of one another, hydrogen, halogen, alkyl or nitro; and
provided that $R_{1a}$ and $R_{2a}$ are not simultaneously hydrogen; and that $R_{4a}$, $R_{5a}$ and $R_{6a}$ are not simultaneously hydrogen;

in the free form or in the form of a pesticidally acceptable salt thereof;

and a 1-arylpyrazole of formula (II):

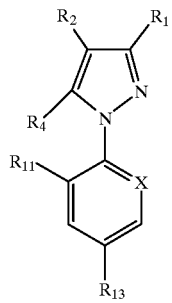

(II)

wherein:
- $R_1$ is CN or methyl;
- $R_2$ is $S(O)_n R_3$;
- $R_3$ is alkyl or haloalkyl;
- $R_4$ is hydrogen, halogen, $-NR_5R_6$, $-C(O)OR_7$, $-S(O)_m R_7$, alkyl, haloalkyl, $-OR_8$, $-N=C(R_9)(R_{10})$ or $-C(O)$alkyl;
- $R_5$ and $R_6$ are, independently of each other, hydrogen, alkyl, haloalkyl, $-C(O)$alkyl, $-C(O)OR_7$ or $-S(O)_r CF_3$; or $R_5$ and $R_6$ form together a divalent alkylene radical which is optionally interrupted by one or more heteroatoms, each of which is preferably oxygen, nitrogen or sulfur;
- $R_7$ is alkyl or haloalkyl;
- $R_8$ is alkyl, haloalkyl or hydrogen;
- $R_9$ is hydrogen or alkyl;
- $R_{10}$ is phenyl or heteroaryl, each of which is optionally substituted by one or more hydroxy, halogen, $-O-$alkyl, $-S-$alkyl, cyano, or alkyl or combinations thereof;
- X is nitrogen or $C-R_{12}$;
- $R_{11}$ and $R_{12}$ are, independently of each other, halogen or hydrogen;
- $R_{13}$ is halogen, haloalkyl, haloalkoxy, $-S(O)_q CF_3$ or $-SF_5$;
- m, n, q, r are, independently of one another, 0, 1 or 2;
- provided that when $R_1$ is methyl, then $R_3$ is haloalkyl, $R_4$ is $NH_2$, $R_{11}$ is Cl, $R_{13}$ is $CF_3$, and X is N;

to manufacture a composition for the control of parasites in or on an animal.

The present invention also relates to a method of cleaning animals in good health comprising the application to the animal of a combination of a compound of formula (I):

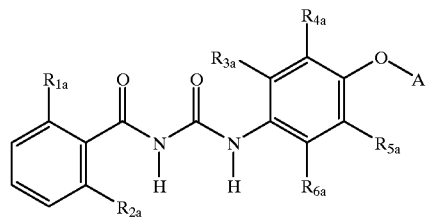

(I)

wherein:
- $R_{1a}$ and $R_{2a}$ are, independently of each other, hydrogen or halogen;
- $R_{3a}$ is hydrogen, chlorine or alkyl;
- $R_{4a}$, $R_{5a}$ and $R_{6a}$ are, independently of one another, alkyl, preferably methyl, hydrogen or halogen; p1 A is G1, G2, G3 or G4:

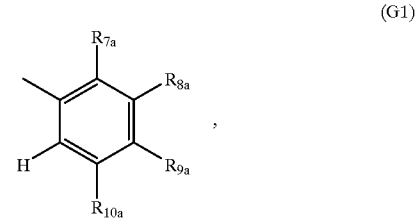

(G1)

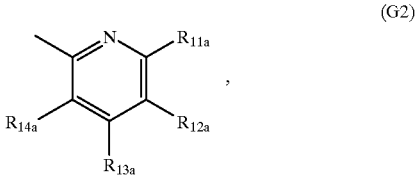

(G2)

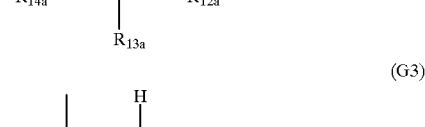

(G3)

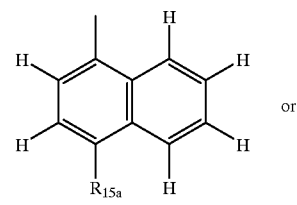

(G4)

wherein
- $R_{7a}$ to $R_{16a}$ are, independently of one another, hydrogen, halogen, alkyl or nitro; and
- provided that $R_{1a}$ and $R_{2a}$ are not simultaneously hydrogen; and that $R_{4a}$, $R_{5a}$ and $R_{6a}$ are not simultaneously hydrogen;

in the free form or in the form of a pesticidally acceptable salt thereof; and a 1-arylpyrazole of formula (II):

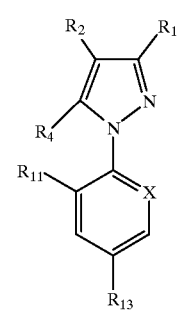

(II)

wherein:
- $R_1$ is CN or methyl;
- $R_2$ is $S(O)_n R_3$;
- $R_3$ is alkyl or haloalkyl;
- $R_4$ is hydrogen, halogen, $-NR_5R_6$, $-C(O)OR_7$, $-S(O)_m R_7$, alkyl, haloalkyl, $-OR_8$, $-N=C(R_9)(R_{10})$ or $-C(O)$alkyl;
- $R_5$ and $R_6$ are, independently of each other, hydrogen, alkyl, haloalkyl, $-C(O)$alkyl, $-C(O)OR_7$ or $-S(O)_r CF_3$; or $R_5$ and $R_6$ form together a divalent alkylene radical which is optionally interrupted by one or more heteroatoms, each of which is preferably oxygen, nitrogen or sulfur;
- $R_7$ is alkyl or haloalkyl;
- $R_8$ is alkyl, haloalkyl or hydrogen;
- $R_9$ is hydrogen or alkyl;
- $R_{10}$ is phenyl or heteroaryl, each of which is optionally substituted by one or more hydroxy, halogen, $-O$—alkyl, $-S$—alkyl, cyano, or alkyl or combinations thereof;
- X is nitrogen or $C$-$R_{12}$;
- $R_{11}$ and $R_{12}$ are, independently of each other, halogen or hydrogen;
- $R_{13}$ is halogen, haloalkyl, haloalkoxy, $-S(O)_q CF_3$ or $-SF_5$;
- m, n, q, r are, independently of one another, 0, 1 or 2;
- provided that when $R_1$ is methyl, then $R_3$ is haloalkyl, $R_4$ is $NH_2$, $R_{11}$ is Cl, $R_{13}$ is $CF_3$, and X is N;
- or a composition comprising the combination to the animal.

The method of cleaning an animal is not a method of treatment of the animal body per se, because:
(a) the animal is in good health and requires no substantial treatment to correct a deficiency of health;
(b) the cleaning of the animal is not intended to be done by veterinary personnel, but by persons interested in the cleaning of the animal; and
(c) the purpose of such cleaning is to avoid unpleasant conditions for humans and the environment which humans inhabit so as to not infest the humans with arthropods carried by the animal.

The present invention also relates to a composition comprising an arthropocidally effective, substantially non-emetic amount of a compound of formula (I) and an acceptable carrier. Acceptable carriers acceptable for the use of the compounds are generally known to the skilled addressee concerned with arthropod control in animals, particularly domestic animals.

A particularly advantageous utility of the instant invention is in the protection of structures from nuisance insects including termites and cockroaches and ants.

The invention also relates to compositions comprising a combination of a compound of formula (I) and the 1-arylpyrazole of formula (II) in association with a pesticidally acceptable adjuvant.

Depending on the intended objectives and the prevailing circumstances, the pesticidal compositions are generally emulsifiable concentrates, suspension concentrates, directly sprayable or dilutable solutions, coatable pastes, dilute emulsions, wettable powders, soluble powders, dispersible powders, wettable powders, dusts, granulates or encapsulations in polymer substances, comprising a compound of formula (I) and a 1-arylpyrazole of formula (II).

The active ingredients are generally used in those compositions in pure form, the solid compounds being typically used in a specific particle size, or preferably together with at least one of the adjuvants customary in formulation technology, for example extenders such as solvents, or solid carriers, or surface-active compounds (surfactants).

Suitable solvents are typically aromatic hydrocarbons or partially hydrogenated aromatic hydrocarbons, preferably the fraction of alkylbenzenes containing 8 to 12 carbon atoms, such as xylene mixtures, alkylated naphthalenes or tetrahydronaphthalene, aliphatic or cycloaliphatic hydrocarbons such as paraffins or cyclohexane; alcohols such as ethanol, propanol or butanol; glycols and their ethers and esters such as propylene glycol, dipropylene glycol ether, diethylene glycol or 2-methoxyethanol or 2-ethoxyethanol; ketones such as cyclohexanone, isophorone or diacetone alcohol, strongly polar solvents such as N-methylpyrrolid-2-one, dimethyl sulfoxide or N,N-dimethylformamide; water, vegetable oils or epoxidized vegetable oils such as rape oil, castor oil, coconut oil or soybean oil or epoxidized rape oil, castor oil, coconut oil or soybean oil, and silicone oils.

The solid carriers typically used for dusts and dispersible powders are usually natural mineral fillers such as calcite, talcum, kaolin, montmorillonite or attapulgite. To improve the physical properties it is also possible to add highly dispersed silicic acids or highly dispersed absorbent polymers. Suitable granulated adsorptive carriers are porous types, including pumice, broken brick, sepiolite or bentonite, and suitable nonsorbent carriers are calcite or sand. In addition, innumerable granulated materials of inorganic or organic nature may be used, especially dolomite or pulverized plant residues.

Another type of solid carrier that may be used in the present invention is a biodegradable polymer, particularly one which degrades inside the animal's body over an extended period of time, preferably one administration per month, more preferably two to three months, even more preferably four to six months, much more preferably seven to eight months, and most preferably nine to twelve months.

Depending on the type of compound to be formulated, suitable surface-active compounds are nonionic, cationic and/or anionic surfactants or mixtures of surfactants preferably having good emulsifying, dispersing and wetting properties. The surfactants listed below shall be regarded merely as exemplary; many more surfactants customarily employed in formulation technology and suitable for use in the practice of the invention are described in the relevant literature.

Nonionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable nonionic surfactants are water-soluble polyadducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of nonionic surfactants are nonylphenol polyethoxyethanols, polyethoxylated castor oil, polyadducts of polypropylene and polyethylene oxide, tributylphenol polyethoxylate, polyethylene glycol and octylphenol polyethoxylate. Fatty acid esters of polyoxyethylene sorbitan, e.g. polyoxyethylene sorbitan trioleate, are also suitable nonionic surfactants.

Cationic surfactants are preferably quaternary ammonium salts carrying, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methyl sulfates or ethyl sulfates. Examples are stearyldimethylammonium chloride and benzyl bis(2-chloroethyl) ethylammonium bromide.

Suitable anionic surfactants may be water-soluble soaps as well as water-soluble synthetic surface-active compounds. Suitable soaps are the alkali metal salts, alkaline earth metal salts and unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil. Further suitable soaps are also the fatty acid methyltaurine salts.

More frequently, however, synthetic surfactants are used, preferably fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and usually contain a $C_8$–$C_{22}$ alkyl radical, which also includes the alkyl moiety of acyl radicals. Typical examples are the sodium or calcium salt of ligninsulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Typical examples of alkylarylsulfonates are the sodium, calcium or triethanolammonium salts of dodecylbenzenesulfonic acid, dibutylnaphthalenesulfonic acid or of a condensate of naphthalenesulfonic acid and formaldehyde. Corresponding phosphates, e.g. salts of the phosphoric acid ester of an adduct of p-nonylphenol with 4 to 14 mol of ethylene oxide, or phospholipids are also suitable.

The compositions will usually comprise 0.1 to 99%, preferably 0.1 to 95% of a combination of the compound of formula (I) and one or more 1-arylpyrazoles of formula (II) and 1 to 99.9%, preferably 5 to 99.9%, of at least one solid or liquid adjuvant; usually they will contain 0 to 25%, preferably 0.1 to 20%, of surfactants (wherein in each case percentages are by weight). Whereas commercial products will preferably be formulated as concentrates, the end user will normally employ dilute formulations having a substantially lower concentration of active ingredient. Particularly preferred formulations will be made up as follows (wherein, throughout, percentages are by weight):

Emulsifiable Concentrates
combination of (I) and (II): 1 to 95%, preferably 5 to 20%
surfactant: 1 to 30%, preferably 10 to 20%
solvent: 5 to 98%, preferably 70 to 85%

Dusts
combination of (I) and (II): 0.1 to 10%, preferably 0.1 to 1%
solid carrier: 99.9 to 90%, preferably 99.9 to 99%

Suspension Concentrates
combination of (I) and (II): 5 to 75%, preferably 10 to 50%
water: 94 to 24%, preferably 88 to 30%
surfactant: 1 to 40%, preferably 2 to 30%

Wettable Powders
combination of (I) and (II): 0.5 to 90%, preferably 1 to 80%
surfactant: 0.5 to 20%, preferably 1 to 15%
solid carrier: 5 to 99%, preferably 15 to 98%

Granules
combination of (I) and (II): 0.5 to 30%, preferably 3 to 15%
solid carrier: 99.5 to 70%, preferably 97 to 85%

The novel compositions may also contain further solid or liquid adjuvants such as stabilizers, e.g. vegetable oils or epoxidized vegetable oils (e.g. epoxidized coconut oil, rapeseed oil or soybean oil), antifoams, e.g. silicone oil, preservatives, viscosity regulators, binders and/or tackers, as well as fertilizers or other chemical agents for obtaining special effects, typically including bactericides, fungicides, nematicides, molluscicides or herbicides.

The compositions of this invention are prepared in known manner; in the absence of adjuvants, typically by grinding, sieving and/or compressing a solid active ingredient or mixture of active ingredients, for example to a specific particle size; and in the presence of at least one adjuvant, for example by intimately mixing and/or grinding the active ingredient or mixture of active ingredients with the adjuvant or adjuvants. The invention also relates to the preparation of the compositions.

The methods of applying the combinations, i.e. the methods of controlling pests at a locus of the indicated type, typically include spraying, atomizing, dusting, coating, dressing, scattering or pouring, selected in accordance with the intended objectives and prevailing circumstances, and the use of the combinations for controlling pests of the indicated type, are further objects of the invention. Typical rates of concentration are in the range from 0.01 to 1000 ppm, preferably from 0.1 to 500 ppm, of active ingredient. The rate of application may vary over a wide range and will depend on the nature of soil, the type of application (e.g. foliar application, seed dressing application to the seed furrow), the cultivated plant, the pest to be controlled, the prevailing climatic conditions and other factors governed by the type of application, time of application and target crop. The rates of application per hectare will usually be from 0.5 g/ha to 2000 g/ha, more particularly from 10 to 1000 g/ha, preferably from 20 to 600 g/ha.

A preferred method of application in the field of plant protection is application to the foliage of the plants (foliar application), the number of applications and the rate of application depending on the risk of infestation by the particular pest. However, the active ingredients can also penetrate the plants through the roots (systemic action) by drenching the locus of the plants with a liquid formulation or by applying the active ingredient in solid form to the locus of the plants, for example to the soil, e.g. in granular form (soil application). In paddy rice crops, such granules may be applied to the flooded rice field.

It is also contemplated that the invention comprises a compound of formula (I) in its free form or a pesticidally acceptable salt thereof and a 1-arylpyrazole of formula (II) for simultaneous, separate or sequential use in the control of pests at a locus.

The compositions of the invention are also suitable for protecting plant propagation material, e.g. seeds such as fruit, tubers or grains, or plant cuttings, against animal pests. The propagation material can be treated with the formulation before planting. Seeds, for example, can be dressed before sowing. The compounds of the invention can also be applied to grains (e.g. by coating), for example by impregnating the grains with a liquid formulation or by coating them with a solid formulation. The composition can also be applied to the locus of planting when planting the propagation material, for example to the seed furrow during sowing. The invention relates also to these methods of treating plant propagation material and to the plant propagation material so treated.

The invention is illustrated by the following non-limiting Examples.

Formulation Examples (%=per cent by weight; ratios=weight ratios)

| Example F1: Emulsifiable concentrate | a) | b) | c) |
|---|---|---|---|
| combination (ratio of compound of formula (I) to a compound (II) 1:1) | 25% | 40% | 50% |
| Ca dodecylbenzenesulfonate | 5% | 8% | 6% |
| polyethoxylated castor oil (36 mol EO) | 5% | — | — |
| tributylphenol polyethoxylate (30 mol EO) | — | 12% | 4% |
| cyclohexanone | — | 15% | 20% |
| xylene mixture | 65% | 25% | 20% |

Emulsions of any desired concentration can be prepared from such concentrates by dilution with water.

|  | a) | b) | c) | d) |
|---|---|---|---|---|
| Example F2: Solutions | | | | |
| combination (2:1) | 80% | 10% | 5% | 95% |
| 2-methoxyethanol | 20% | — | — | — |
| polyethylene glycol MW 400 | — | 70% | — | — |
| N-methyl-2-pyrrolidone | — | 20% | — | — |
| epoxidized coconut oil | — | — | 1% | 5% |
| petroleum spirit (boiling range 160–190° C.) | — | — | 94% | — |
| Example F3- Granulates | | | | |
| combination (1:10) | 5% | 10% | 8% | 21% |
| kaolin | 94% | — | 79% | 54% |
| highly dispersed silica | 1% | — | 13% | 7% |
| attapulgite | — | 90% | — | 18% |

The solutions are suitable for use in the form of microdrops.

The active ingredients are dissolved in dichloromethane, the solution is sprayed onto the carrier and the solvent is subsequently evaporated in vacuo.

| Example F4- Dusts | a) | b) |
|---|---|---|
| combination (1:5) | 2% | 5% |
| highly dispersed silica | 1% | 5% |
| talcum | 97% | — |
| kaolin | — | 90% |

Ready-to-use dusts are obtained by intimately mixing the carriers with the active ingredients.

| Example F5: Wettable powders | a) | b) | c) |
|---|---|---|---|
| combination (1:1) | 25% | 50% | 75% |
| sodium ligninsulfonate | 5% | 5% | — |
| sodium lauryl sulfate | 3% | — | 5% |
| sodium diisobutylnaphthalene-sulfonate | — | 6% | 10% |
| octylphenol polyethoxylate (7–8 mol EO) | — | 2% | — |
| highly dispersed silica | 5% | 10% | 10% |
| kaolin | 62% | 27% | — |

The active ingredients are mixed with the additives, and the mixture is ground thoroughly in a suitable mill. This gives wettable powders which can be diluted with water to give suspensions of any desired concentrations.

| Example F6: Emulsifiable concentrate | |
|---|---|
| combination (1:1) | 10% |
| octylphenol polyethoxylate (4–5 mol EO) | 3% |
| calcium dodecylbenzenesulfonate | 3% |
| polyethoxylated castor oil (36 mol EO) | 4% |
| cyclohexanone | 30% |
| xylene mixture | 50% |

Emulsions of any desired concentration can be prepared from this concentrate by dilution with water.

| Example F7: Dusts | a) | b) |
|---|---|---|
| combination (1:2) | 5% | 8% |
| talcum | 95% | — |
| kaolin | — | 92% |

Ready-to-use dusts are obtained by mixing the active ingredients with the carrier and grinding the mixture on a suitable mill.

| Example F8: Extruder granules | |
|---|---|
| combination (1:3) | 10% |
| sodium ligninsulfonate | 2% |
| carboxymethyl cellulose | 1% |
| kaolin | 87% |

The active ingredients are mixed with the additives, and the mixture is ground and moistened with water. This mixture is extruded, granulated and subsequently dried in a stream of air.

| Example F9: Coated granulates | |
|---|---|
| combination (1:1) | 3% |
| polyethylene glycol (MW 200) | 3% |
| kaolin | 94% |

In a mixer, the finely ground active ingredients are applied uniformly to kaolin, which has been moistened with polyethylene glycol, to give dust-free coated granules.

| Example F10: Suspension concentrate | |
|---|---|
| combination (2:1) | 40% |
| ethylene glycol | 10% |
| nonylphenol polyethoxylate (15 mol EO) | 6% |
| sodium ligninsulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredients are mixed intimately with the additives to give a suspension concentrate from which suspensions of any desired concentration can be prepared by dilution with water.

It is often more expedient to formulate the compound of formula (I) and one of the 1-arylpyrazoles of formula (II) singly and then to mix them in the desired ratio in the applicator as a tank mixture in water shortly before application.

Biological Examples (%=per cent by weight, unless otherwise indicated)

A synergistic effect is always obtained whenever the activity of the combination of the compound of formula (I) with one of the pesticides (II) is greater than the sum of the activities of the individually applied compounds.

For example, the expected pesticidal activity We of a given combination of two pesticides can be calculated as follows (q.v. COLBY, S. R., "Calculating synergistic and antagonstic response of herbicide combinations". Weeds 15, pages 20–22, 1967):

$$We = X + \frac{Y \cdot (100 - X)}{100}$$

wherein

X= Percentage mortality, compared with untreated controls, after treatment with the compound of formula (I) at a rate of application of p g/hectare (=0%).

Y= Percentage mortality, compared with untreated controls, after treatment with a arylpyrazole of formula (II) at a rate of application of q kg/hectare.

We= The expected pesticidal activity (percentage mortality compared with untreated controls) after treatment with the compound of formula (I) and a 1-arylpyrazole (II) at a rate of application of p+q kg a.i./ha.

If the actually observed value is greater than the expected value We, then there is synergism.

The synergistic effect of the combination of a compound of formula (I) with one of the 1-arylpyrazoles of formula (II) is demonstrated in the following non-limiting Examples.

EXAMPLE 1

Action against *Spodoptera eridania*

Artificial growth medium is treated with Compound C at rates of 0.5, 0.25, 0.125, 0.06, and 0.03 ppm. Artificial growth medium is treated with Compound A at rates of 8, 4, 2, 1 and 0.5 ppm. Artificial growth medium is treated with the following rate combinations of Compound C and Compound A: (0.5+8); (0.25+4); (0.125+2); (0.06+1); and (0.03+0.5). Larvae of *Spodoptera eridania* are placed in the medium and allowed to stay for days. Mortality is measured at 4 and 7 days after the larvae are allowed to begin to feed. The following results which show synergism in three of five rates are obtained at 4 days after treatment:

| Rate (ppm)/% Mortality of Compound C | Rate (ppm)/% Mortality of fipronil | We | Actual Mortality of Compound C and fipronil |
|---|---|---|---|
| 0.5/80 | 8/100 | 100 | 80 |
| 0.25/10 | 4/30 | 37 | 40 |
| 0.125/10 | 2/0 | 10 | 40 |
| 0.06/10 | 1/10 | 19 | 30 |
| 0.03/0 | 0.5/0 | 0 | 0 |

The following results, which show synergy at two of the five rates, are obtained at 7 days after treatment (DAT):

| Rate (ppm)/% Mortality of Compound C | Rate (ppm)/% Mortality of fipronil | We | Actual Mortality of Compound C and fipronil |
|---|---|---|---|
| 0.5/100 | 8/100 | 100 | 100 |
| 0.25/100 | 4/70 | 100 | 100 |
| 0.125/80 | 2/40 | 88 | 100 |
| 0.06/80 | 1/30 | 86 | 100 |
| 0.03/0 | 0.5/20 | 20 | 20 |

This test illustrates the general synergism of the invention.

EXAMPLE 2

The procedure of Example 1 was followed using cotton leaves sprayed to runoff with combination using the rates shown in the following tables. The tables indicate individual data at the date after treatment indicated.

| Rate (ppm)/% Mortality of Compound C | Rate (ppm)/% Mortality of Compound B |
|---|---|
| 2 days after Treatment | |
| 0.4/20 | 500/0 |
| 0.1/10 | 250/0 |
| 0.025/0 | |
| 0.006/0 | |
| 0.0015/0 | |
| 4 days after Treatment | |
| 0.4/100 | 500/10 |
| 0.1/40 | 250/0 |
| 0.025/0 | |
| 0.006/0 | |
| 0.0015/0 | |
| 5 days after Treatment | |
| 0.4/100 | 500/10 |
| 0.1/70 | 250/0 |
| 0.025/0 | |
| 0.006/0 | |
| 0.0015/0 | |

The following table indicates the results obtained with mixtures of Compounds B and C.

| Rate (ppm) Compound C | Rate (ppm) Compound B | We 2 DAT | Actual 2 DAT | We 4 DAT | Actual 4 DAT | We 5 DAT | Actual 5 DAT |
|---|---|---|---|---|---|---|---|
| 0.4 | 500 | 40 | 20 | 100 | 100 | 100 | 100 |
| 0.1 | 500 | 10 | 0 | 46 | 60 | 77 | 100 |
| 0.025 | 500 | 0 | 0 | 10 | 20 | 10 | 30 |
| 0.006 | 500 | 0 | 0 | 10 | 0 | 10 | 10 |
| 0.0015 | 500 | 0 | 0 | 10 | 0 | 10 | 0 |
| 0.4 | 250 | 40 | 0 | 100 | 100 | 100 | 100 |
| 0.1 | 250 | 10 | 0 | 40 | 30 | 70 | 80 |
| 0.025 | 250 | 0 | 0 | 0 | 20 | 0 | 40 |
| 0.006 | 250 | 0 | 0 | 0 | 0 | 0 | 30 |
| 0.0015 | 250 | 0 | 0 | 0 | 0 | 0 | 0 |

EXAMPLE 3

In the test of Example 2, after five days, a general and substantial reduction in damage to the leaves is observed for the combination. Data for this test is shown in the following table:

| Concentration of Compound C (ppm) | Concentration of Compound B (ppm) | Per cent Feeding Damage |
|---|---|---|
| 0 | 0 | 60 |
| 0 | 250 | 60 |
| 0 | 500 | 50 |
| 0.4 | 0 | 2 |
| 0.1 | 0 | 10 |
| 0.025 | 0 | 60 |
| 0.006 | 0 | 60 |
| 0.0015 | 0 | 60 |
| 0.4 | 500 | 2 |
| 0.1 | 500 | 5 |
| 0.025 | 500 | 20 |
| 0.006 | 500 | 30 |
| 0.0015 | 500 | 60 |
| 0.4 | 250 | 2 |
| 0.1 | 250 | 5 |
| 0.025 | 250 | 25 |
| 0.006 | 250 | 30 |
| 0.0015 | 250 | 40 |

EXAMPLE 4

Cats, housed in cages with wire mesh bottoms, are infested with about 50 fleas at 1 week intervals for the course of the study. One day after the first infestation, the cats are treated by a subcutaneous injection of a mixture of Compound C at a rate of 10 mg/kg and Compound B at a rate of 20 mg/kg in polyethylene glycol. One day later, and two days after each weekly infestation for the course of the study, sweepings of debris which are collected on plywood boards placed beneath the cages are combined with flea rearing media and evaluated for development of flea progeny. Adult fleas on the cats are counted weekly, two days after each infestation, for the duration of the study by combing the cats. Greater than 95% control of development of flea progeny and >90% control of flea adults is maintained for 26 and 52 weeks post treatment.

EXAMPLE 5

Cats, housed in cages with wire mesh bottoms are infested with about 50 fleas at 1 week intervals for the course of the study. One day after the first infestation, the cats are treated by oral gavage via stomach tube of a mixture of Compound C at a rate of 20 mg/kg and Compound A at a rate of 20 mg/kg in a 1:1 v/v DMSO/corn oil mixture. One day later, and two days after each weekly infestation for the course of the study, sweepings of debris, which are collected on plywood boards placed beneath the cages, are combined with flea rearing media and evaluated for development of flea progeny. Adult fleas on the cats are counted weekly, two days after each infestation, for the duration of the study by combing the cats. Greater than 95% control of development of flea progeny and >90% control of flea adults is maintained for 26 and 52 weeks post treatment.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A pesticidal combination comprising a combined synergistic pesticidally effective amount of:
   (a) 1-[4-(2,4-dichlorophenoxy)-2,5-dimethyl-3-chlorophenyl]-3-(2,6-difluorobenzoyl)urea, in the free form or in the form of a pesticidally acceptable salt thereof; and
   (b) 5-amino-3-cyano-1-(2,6-dichloro-4-trifluoromethylphenyl)-4-trifluoromethylsulfinylpyrazole or 5-amino-3-cyano-1-(2,6-dichloro-4-trifluoromethylphenyl)-4-ethylsulfinylpyrazole;
   the weight ratio of (a) to (b) being from 1:50 to 50:1.

2. A combination according to claim 1, wherein (b) is 5-amino-3-cyano-1-(2,6-dichloro-4-trifluoromethylphenyl)-4-trifluoromethylsulfinylpyrazole.

3. A combination according to claim 1, wherein the weight ratio of (a) to (b) is from 10:1 to 1:10.

4. A combination according to claim 2, wherein the weight ratio of (a) to (b) is from 10:1 to 1:10.

5. A combination according to claim 3, wherein the weight ratio of (a) to (b) is from 5:1 to 1:5.

6. A combination according to claim 4, wherein the weight ratio of (a) to (b) is from 5:1 to 1:5.

7. A combination according to claim 5, wherein the weight ratio of (a) to (b) is from 2:1 to 1:2.

8. A combination according to claim 6, wherein the weight ratio of (a) to (b) is from 2:1 to 1:2.

9. A combination according to claim 7, wherein the weight ratio of (a) to (b) is 1:1.

10. A combination according to claim 8, wherein the weight ratio of (a) to (b) is 1:1.

11. A combination according to claim 1, which is long-acting.

12. A combination according to claim 2, which is long-acting.

13. A combination according to claim 1, wherein the combined amount of (a) and (b) is sufficient to produce an antifeeding effect in pests.

14. A combination according to claim 2, wherein the combined amount of (a) and (b) is sufficient to produce an antifeeding effect in pests.

15. A pesticidal combination comprising a combined synergistic pesticidally effective amount of:
(a) 1-[4-(2,4-dichlorophenoxy)-2,5-dimethyl-3-chlorophenyl]-3-(2,6-difluorobenzoyl)urea, in the free form or in the form of a pesticidally acceptable salt thereof; and
(b) 5-amino-3-cyano-1-(2,6-dichloro-4-trifluoromethylphenyl)-4-trifluoromethylsulfinylpyrazole or 5-amino-3-cyano-1-(2,6-dichloro-4-trifluoromethylphenyl)-4-ethylsulfinylpyrazole;
the weight ratio of (a) to (b) being from 1:625 to 1:333,334.

16. A combination according to claim 7, wherein (b) is 5-amino-3-cyano-1-(2,6-dichloro-4-trifluoromethylphenyl)-4-ethylsulfinylpyrazole.

17. A combination according to claim 15, which is long-acting.

18. A combination according to claim 16, which is long-acting.

19. A combination according to claim 15, wherein the combined amount of (a) and (b) is sufficient to produce an antifeeding effect in pests.

20. A combination according to claim 16, wherein the combined amount of (a) and (b) is sufficient to produce an antifeeding effect in pests.

21. A pesticidal composition comprising a synergistic pesticidally effective amount of a combination according to claim 1, and a pesticidally acceptable adjuvant therefor.

22. A pesticidal composition comprising a synergistic pesticidally effective amount of a combination according to claim 2 and a pesticidally acceptable adjuvant therefor.

23. A pesticidal composition comprising a synergistic pesticidally effective amount of a combination according to claim 13 and a pesticidally acceptable adjuvant therefor.

24. A pesticidal composition comprising a synergistic pesticidally effective amount of a combination according to claim 14 and a pesticidally acceptable adjuvant therefor.

25. A pesticidal composition comprising a synergistic pesticidally effective amount of a combination according to claim 15 and a pesticidally acceptable adjuvant therefor.

26. A pesticidal composition comprising a synergistic pesticidally effective amount of a combination according to claim 16 and a pesticidally acceptable adjuvant therefor.

27. A pesticidal composition comprising a synergistic pesticidally effective amount of a combination according to claim 19 and a pesticidally acceptable adjuvant therefor.

28. A pesticidal composition comprising a synergistic pesticidally effective amount of a combination according to claim 20 and a pesticidally acceptable adjuvant therefor.

29. A method of controlling pests at a locus comprising applying to said pests or to their locus an amount which is synergistically pesticidally effective, in combination, of:
(a) 1-[4-(2,4-dichlorophenoxy)-2,5-dimethyl-3-chlorophenyl]-3-(2,6-difluorobenzoyl)urea, in the free form or in the form of a pesticidally acceptable salt thereof; and
(b) 5-amino-3-cyano-1-(2,6-dichloro-4-trifluoromethylphenyl)-4-trifluoromethylsulfinylpyrazole or 5-amino-3-cyano-1-(2,6-dichloro-4-trifluoromethylphenyl)-4-ethylsulfinylpyrazole;
the weight ratio of (a) to (b) being from 1:50 to 50:1.

30. A method according to claim 29, wherein (b) is 5-amino-3-cyano-1-(2,6-dichloro-4-trifluoromethylphenyl)-4-trifluoromethylsulfinylpyrazole.

31. A method according to claim 29, wherein the weight ratio of (a) to (b) is from 10:1 to 1:10.

32. A method according to claim 30, wherein the weight ratio of (a) to (b) is from 10:1 to 1:10.

33. A method according to claim 31, wherein the weight ratio of (a) to (b) is from 5:1 to 1:5.

34. A method according to claim 32, wherein the weight ratio of (a) to (b) is from 5:1 to 1:5.

35. A method according to claim 32, wherein the weight ratio of (a) to (b) is from 2:1 to 1:2.

36. A method according to claim 34, wherein the weight ratio of (a) to (b) is from 2:1 to 1:2.

37. A method according to claim 35, wherein the weight ratio of (a) to (b) is 1:1.

38. A method according to claim 36, wherein the weight ratio of (a) to (b) is 1:1.

39. A method according to claim 29, which is long-acting.

40. A method according to claim 30, which is long-acting.

41. A method according to claim 29, wherein the amount of (a) and (b) applied is sufficient in combination to produce an antifeeding effect in said pests.

42. A method according to claim 30, wherein the amount of (a) and (b) applied is sufficient in combination to produce an antifeeding effect in said pests.

43. A method according to claim 29, wherein the locus is an animal.

44. A method according to claim 30, wherein the locus is an animal.

45. A method according to claim 43, wherein (a) and (b) are administered orally.

46. A method according to claim 44, wherein (a) and (b) are administered orally.

47. A method according to claim 43, wherein (a) and (b) are administered by subcutaneous injection or as an implant.

48. A method according to claim 44, wherein (a) and (b) are administered by subcutaneous injection or implantation.

49. A method according to claim 43, wherein (a) is administered in an amount of from 1 to 100 mg per kg of body weight of animal and (b) is administered in an amount of from 5 to 50 mg per kg of body weight of the animal.

50. A method according to claim 49, wherein (a) is administered in an amount of from 10 to 50 mg per kg of body weight of the animal.

51. A method according to claim 49, wherein (a) is administered in an amount of from 10 to 20 mg per kg of body weight of the animal.

52. A method according to claim 49, wherein (b) is administered in an amount of from 10 to 30 mg per kg of body weight of the animal.

53. A method of controlling pests at a locus comprising applying to said pests or to their locus an amount which is synergistically pesticidally effective, in combination, of:
(a) 1-[4-(2,4-dichlorophenoxy)-2,5-dimethyl-3-chlorophenyl]-3-(2,6-difluorobenzoyl)urea, in the free form or in the form of a pesticidally acceptable salt thereof, and
(b) 5-amino-3-cyano-1-(2,6-dichloro-4-trifluoromethylphenyl)-4-trifluoromethylsulfinylpyrazole or 5-amino-3-cyano-1-(2,6-dichloro-4-trifluoromethylphenyl)-4-ethylsulfinylpyrazole;

the weight ratio of (a) to (b) being from 1:625 to 1:333,334.

54. A method according to claim 53, wherein (b) is 5-amino-3-cyano-1-(2,6-dichloro-4-trifluoromethylphenyl)-4-ethylsulfinylpyrazole.

55. A method according to claim 53, which is long-acting.

56. A method according to claim 54, which is long-acting.

57. A method according to claim 53, wherein the amount of (a) and (b) applied is sufficient in combination to produce an antifeeding effect in said pests.

58. A method according to claim 54, wherein the amount of (a) and (b) applied is sufficient in combination to produce an antifeeding effect in said pests.

59. A method according to claim 53, wherein the locus is an animal.

60. A method according to claim 54, wherein the locus is an animal.

61. A method according to claim 59, wherein (a) and (b) are administered orally.

62. A method according to claim 60, wherein (a) and (b) are administered orally.

63. A method according to claim 59, wherein (a) and (b) are administered by subcutaneous injection or implantation.

64. A method according to claim 60, wherein (a) and (b) are administered by subcutaneous injection or implantation.

* * * * *